United States Patent [19]
Stella et al.

[11] Patent Number: 5,610,143
[45] Date of Patent: Mar. 11, 1997

[54] ANTIBIOTICS GE 37468 A, B AND C

[75] Inventors: Sergio Stella, Legnano; Nicoletta Montanini, Carpiano; Francis J. LeMonnier, Saronno; Luigi Colombo, Malnate; Enrico Selva, Gropello Cairoli, all of Italy; Maurizio Denaro, Cincinnati, Ohio

[73] Assignee: Gruppo Lepetit S.p.A., Varese, Italy

Related U.S. Application Data

[63] Continuation-in-part of PCT/EP93/03541, Dec. 15, 1993.

[21] Appl. No.: 493,043
[22] Filed: Jun. 21, 1995
[51] Int. Cl.$^6$ .............................. C07K 5/00; A61K 37/02
[52] U.S. Cl. .............................................. 514/18; 530/331
[58] Field of Search ................................ 530/331; 514/18; 540/456

[56] References Cited

PUBLICATIONS

Stella et al. Chemical Abstract 123:193175 (1995).
Stella et al. Chemical Abstract 122:128491 (1994).

*Primary Examiner*—Johann Richter
*Assistant Examiner*—Ebenezer Sackey
*Attorney, Agent, or Firm*—J. Michael Dixon

[57] ABSTRACT

The present invention is directed to new antibiotic substances denominated antibiotics GE 37468 A, B and C, their addition salts with bases, the pharmaceutical compositions thereof and their use as medicaments, particularly in the treatment of infectious diseases involving microorganisms susceptible to them.

The compounds of the invention are also active as growth promotant agents in animals, such as poultry, swine, ruminants, etc.

5 Claims, 4 Drawing Sheets

ANTIBIOTICS GE 37468 A, B AND C

Ths application is a continuation-in-part of PCT/EP93/03541, designating the United States of America and having the International filing date of Dec. 15, 1993.

The present invention is directed to new antibiotic substances denominated antibiotics GE 37468 A, B and C, their addition salts with bases, the pharmaceutical compositions thereof and their use as medicaments, particularly in the treatment of infectious diseases involving microorganisms susceptible to them.

The compounds of the invention are also active as growth promotant agents in animals, such as poultry, swine, ruminants, etc.

Another object of the invention is a process for preparing antibiotics GE 37468 A, B and C which includes culturing *Streptomyces sp*. GE 37468 ATCC 55365 or an antibiotics GE 37468 producing variant or mutant thereof and isolating the antibiotics of the invention from the mycelium and/or the fermentation broths.

*Streptomyces sp*. GE 37468 ATCC 55365 was isolated from a soil sample and deposited on Oct. 6, 1992 with the American Type Culture Collection (ATCC), 12301 Parklawn Drive, Rockville, Md. 20852 Maryland, U.S.A., under the provisions of the Budapest Treaty.

The strain has been accorded accession number ATCC 55365.

While antibiotic GE 37468A is a direct result of the metabolic pathway of the above mentioned microbial strain, antibiotics GE 37468 B and C appear to be produced mainly by degradation of the above mentioned antibiotic GE 37468A which occurs during the recovery and isolation procedures following the fermentation stage. As a matter of fact, although it cannot be excluded that minor amounts of the two products are directly produced as metabolites of the microbial strain, their amount increases substantially with the working of the fermentation broth for the isolation and recovery of the fermentation products.

The production of antibiotics GE 37468A, B and C, is achieved by cultivating a Streptomyces strain capable of producing it, i.e. *Streptomyces sp*. GE 37468 ATCC 55365 or an antibiotics GE 37468 producing variant or mutant thereof, under aerobic conditions in an aqueous nutrient medium containing assimilable sources of carbon, nitrogen and inorganic salts, and isolating the antibiotic products from the fermentation batch. Many of the nutrient media usually employed in the fermentation art can be used, however certain media are preferred. Preferred carbon sources are glucose, mannose, galactose, starch, corn meal and the like. Preferred nitrogen sources are ammonia, nitrates, soybean meal, peptone, meat extract, yeast extract, tryprone, aminoacids, and the like. Among the inorganic salts which can be incorporated in the culture media there are the customary soluble salts capable of yielding sodium, potassium, iron, zinc, cobalt, magnesium, calcium, ammonium, chloride, carbonate, sulfate, phosphate, nitrate and the like ions.

Ordinarily, the antibiotic-producing strain is pre-cultured in a shake flask, then the culture is used to inoculate jar fermentors for production of substantial quantities of the antibiotic substances. The medium used for the pre-culture can be the same as that employed for larger fermentations, but other media can also be employed. The "antibiotics GE 37468" (with this generic term are cumulatively designated all three products mentioned above) producing-strain can be grown at temperatures between 20° C. and 40° C., preferably between 24° C. and 35° C.

During fermentation, the antibiotics GE 37468 production can be monitored by testing broth or mycelial extract samples for antibiotic activity, for instance, by bioassays or TLC or HPLC procedures.

Sensitive organisms to antibiotics GE 37468 such as *Bacillus subtilis* and *S. aureus* can be used as test organisms. The bioassay is conveniently performed by the agar diffusion method on agar plates. Maximum production of antibiotic activity generally occurs between the second and the fifth day of fermentation.

The antibiotic activity is produced by cultivating the strain *Streptomyces sp*. GE 37468 ATCC 55365, or an antibiotics GE37468 producing mutant or variant thereof mainly resides in the mycelium.

CHARACTERIZATION OF STRAIN *Streptomyces sp*. GE 37468 ATCC 55365

Cell-Wall Characterization

The enantiomeric form of the cell-wall amino acid (2,6-diaminopimelic acid) was determined using thin layer chromatography following the method of Staneck and Roberts (Staneck J. L., Roberts G. D., "Simplified approach to identification of aerobic actinomycetes by thin layer chromatography" Applied Microbiology 1974; 28: 226–231). Fatty acid composition was assessed by GC/MS analysis of the methyl esters (FAMEs) prepared using the method of Jantzen (Jantzen E., "Analysis of Cellular Components in Bacterial Classification and Diagnosis", Gas Chromatography/Mass Spectrometry—Applications in Microbiology, Eds. G. Odham, L. Larsson, P-A Mardh Plenum Press, New York 1984).

The chemical analysis showed that strain *Streptomyces sp*. GE 37468 ATCC 55365 contains LL-2,6-diaminopimelic acid; meso-2,6-diaminopimelic acid was not detected. The fatty acid profile showed major amounts of saturated, iso and anteiso-fatty acids.

NUTRITIONAL AND BIOCHEMICAL CHARACTERIZATION a) Macromorphology and Biochemical Tests

*Streptomyces sp*. GE 37468 ATCC 55365 was grown in V6 liquid medium having the following composition:

| | |
|---|---|
| Glucose | 20 g/l |
| Beef extract | 5 g/l |
| Yeast extract | 5 g/l |
| Bacto-peptone | 5 g/l |
| Casamino acids | 3 g/l |
| NaCl | 1.5 g/l | for four days. The mycelium was harvested by centrifugation and washed twice in sterile ¼ strength Ringer's solution (OXOID), containing small glass beads (2 mm) to fragment the mycelium. Subsequently, sufficient Ringer's solution was added to the mycelium to provide a suitable inoculum ($A_{414}$=1.8). Aliquots of the suspension were streaked in a cross-hatched manner onto various media recommended by Shirling and Gottlieb (Shirling E. B., and Gottlieb D. "Method for characterization of Streptomyces species", Int. J. Syst. Bacteriol. 1966; 16: 313–340), and several media recommended by Waksman (Waksman S. A., "The Actinomycetes", 1961; Vol. 2: 328–334, The Williams and Wilkins Co., Baltimore). The ability to use a variety of carbohydrates as a carbon and energy source was determined in ISP8

(Shirling and Gottlieb, ibid) medium containing the carbon source at a final concentration of 2% (w/v). All media were incubated at 28° C. for four days. Colour was assessed in natural daylight, using the Colour Atlas of Maerz and Paul (Maerz A. and Paul M. R., "A Dictionary of Colour, 2nd edition, McGraw-Hill Book Co. Inc., New York 1950).

Colonial appearance, substrate and aerial mycelium colour and pigment production for strain *Streptomyces sp.* GE 37468 ATCC 55365 are recorded in Table I. Physiological characteristics of the strain are presented in Table II. The ability to utilize various carbohydrates for growth is shown in Table III.

TABLE I

GROWTH CHARACTERISTICS OF
*Streptomyces sp.* GE 37468 ATCC 55365

| MEDIUM | GROWTH | MORPHOLOGY | COLOUR [NAME, CODE] |
|---|---|---|---|
| ISP 2 | +++ | highly convoluted appearance; glutinous; smooth; edge entire; aerial mycelium present - well developed, floccose, white; no diffusible pigment production | Light beige, 11-L-2 |
| ISP 3 (Oatmeal) | +++ | highly convoluted appearance at the center with smooth edges; glutinous; edge entire; aerial mycelium not produced; no diffusible pigment production | White/opaque |
| Glycerol-Asparagine Medium ISP 5 | +++ | highly convoluted appearance at the center with smooth edges; glutinous; edge entire; aerial mycelium not produced; no diffusible pigment production | Dark ivory 10-D-2 |
| Hickey & Tresner | +++ | highly convoluted appearance; glutinous where aerial mycelium absent; edge entire; aerial mycelium appeared flat and velvety; white; brown [15-J-12] diffusible pigment produced | Brown 14-A-5 Deauville |
| Bennett's | +++ | highly convoluted appearance; glutinous; edge entire; aerial mycelium poorly developed at intersections of streaks; white; diffusible pigment produced | Cream 9-G-2 |
| Czapek-Glucose | +++ | diffuse convolutions; smooth; glutinous; edge entire; aerial mycelium not produced; no diffusible pigment production | White/opaque |
| Glucose-asparagine | +++ | very convoluted, but dim use in appearance, at the center with smooth sides; glutinous; smooth edge; aerial mycelium not produced; no diffusible pigment production | White 10-B-1 Oyster white |
| Nutrient | +++ | convoluted appearance; matt; edge entire; aerial mycelium not produced; no diffusible pigment production | Light beige 11-C-2 Ecru beige |
| Potato | +++ | highly convoluted appearance; matt; smooth edge; extensive aerial mycelium, white with velvety appearance; oil droplets also present; brown [16-A-12, Bistra] diffusible pigment produced | Light beige 11-F-3 |
| Starch ISP 4 | +++ | wrinkled center; smooth and glutinous; smooth, matt sides; edge entire; aerial mycelium not produced; no diffusible pigment production | White/opaque |
| Peptone Yeast Extract Iron ISP 6 | +++ | highly convoluted appearance; glutinous; smooth; edge entire; aerial mycelium not produced; brown [16-A-12, Bistra] diffusible pigment produced | Grey 32-A-1 |
| Tyrosine ISP 7 | +++ | highly convoluted appearance at the center with smooth edges; glutinous; edge entire; aerial mycelium not produced; brown [16-H-2, Bronzesheen] poorly diffused pigment produced | Light Brown/grey 15-A-5 Log Cabin |
| Calcium malate | ++ | weakly developed convolutions; little spread from area of streak; glutinous; edge entire; aerial | White/opaque |

TABLE I-continued

GROWTH CHARACTERISTICS OF
Streptomyces sp. GE 37468 ATCC 55365

| MEDIUM | GROWTH | MORPHOLOGY | COLOUR [NAME, CODE] |
|---|---|---|---|
| Skimmed milk | +++ | mycelium not produced; no diffusible pigment production highly convoluted appearance at the center with smooth sides; glutinous; edge entire; aerial mycelium not produced; no diffusible pigment production; discoloration at growing edge | Brown 15-A-6 Beaver |
| Soil Extract | +++ | barely visible surface mycelium; edge entire; good aerial mycelium development; floccose, white, with an appearance like glass wool; no diffusible pigment production | White |
| Egg albumin | +++ | wrinkled center, smooth and glutinous; smooth, matt sides; edge entire; aerial mycelium not produced; no diffusible pigment production | White/opaque |
| Water | +++ | weakly developed convolutions; little spread from area of streak; glutinous; edge entire; moderate aerial mycelium development, floccose, white, with appearance like glass wool; no diffusible pigment production | White/opaque |
| Czapek sucrose | +++ | very convoluted, but diffuse in appearance; matt; edge feathered; aerial mycelium not produced; no diffusible pigment production | White/opaque |
| Potato Glucose | +++ | highly convoluted appearance; glutinous; dimpled; edge entire; aerial mycelium not produced; no diffusible pigment production | Brown 13-L-8 Buckthorn |
| Oatmeal (mod) | +++ | very convoluted but diffuse in appearance; glutinous where aerial mycelium absent; edge entire; weak aerial mycelium development, floccose; white; no diffusible pigment production | Light beige 11-E-4 Maple |
| Sabouraud | +++ | highly convoluted appearance; glutinous; smooth; edge entire; aerial mycelium not produced; no diffusible pigment production | Light beige 11-B-3 Champagne |

++: moderate growth; +++: good growth
ISP Numbers refer to the media of Shirling and Gottlieb (International Streptomyces Project codes)

TABLE II

PHYSIOLOGICAL TESTS

| Test | Reaction |
|---|---|
| Calcium malate digestion | negative |
| Gelatin liquefaction | positive |
| Hydrogen sulphide production | positive |
| Milk peptonisation | negative |
| Milk coagulation | negative |
| Nitrate reduction (aerobic) | negative |
| Starch hydrolysis | positive |
| Tyrosine reaction (Melanin) | positive |

TABLE III

CARBOHYDRATE UTILISATION

| CARBON SOURCE | GROWTH |
|---|---|
| Arabinose | +++ |
| Cellobiose | +++ |
| Cellulose | $+^n$ |
| Fructose | +++ |
| Galactose | +++ |
| Glucose | +++ |
| Inositol | +++ |
| Lactose | +++ |
| Maltose | +++ |
| Mannitol | +++ |
| Mannose | +++ |
| Raffinose | +++ |
| Rhamnose | +++ |
| Ribose | +++ |

TABLE III-continued

| CARBOHYDRATE UTILISATION | |
|---|---|
| CARBON SOURCE | GROWTH |
| Salicin | +++ |
| Sucrose | +++p |
| Xylose | +++ |

+++: good growth; ++: moderate growth; +: weak growth; —:no growth; p: poor aerial mycelium development; n: no aerial mycelium development b) Micromorphology In liquid culture (V6 medium), no fragmentation of the mycelium was observed after four days' growth at 28° C.

Microscopic examination of the strain on soil extract agar after four days' incubation at 28° C. revealed extensively branched vegetative hyphae (≈1.1 μm in diameter). No fragmentation was observed. The aerial mycelium contained chains of spores, in both retinaculiaperti (spirals with 1–2 loops) and rectiflexible (straight to flexuous) formation.

c) Identification

On the basis of cell-wall composition, macro- and micromorphological examination, the strain GE 37468 was assigned to the genus Streptomyces.

As with other microorganisms, the characteristics of the antibiotics GE37468 producing strain are subject to variation. For example, artificial variants and mutants of the strain can be obtained by treatment with various known mutagens, such as U.V. rays, X-rays, high frequency waves, radioactive rays, and chemicals such as nitrous acid, N-methyl-N'-nitro-N-nitrosoguanidine, and many others. All natural and artificial variants and mutants which belong to a species of the genus Streptomyces and produce antibiotics GE37468 are deemed equivalent to the strain designated with the code ATCC 55365 for the purposes of this invention and are contemplated to be within the scope of this invention.

The recovery and isolation of antibiotics GE37468 from the mycelium of the producing microorganism is conducted according to known per se techniques such as extraction with solvents, precipitation by adding non-solvents or by changing the pH of the solution, partition chromatography, reverse-phase partition chromatography, ion-exchange chromatography, molecular exclusion chromatography and the like.

A preferred procedure for recovering and isolating the antibiotic substances of the invention from the mycelium includes extracting the filtered or centrifugated mycelium with a water-miscible organic solvent, concentrating the extracts and recovering the crude antibiotic substance by precipitation, optionally with the addition of a precipitating agent, by extraction of the concentrated aqueous residue with a water-immiscible organic solvent or by adsorption chromatography followed by elution of the desired products from the adsorption matrix.

The term "water-miscible solvent" as used in this application, is intended to have the meaning currently given in the art to this term and refers to solvents that, at the conditions of use, are miscible with water in a reasonably wide concentration range.

Examples of water-miscible organic solvents that can be used in the extraction of the antibiotic substances of the invention from the mycelial mass are: lower alkanols, e.g. $(C_1–C_3)$alkanols such as methanol, ethanol and propanol; phenyl$(C_1–C_3)$alkanols such as benzyl alcohol; lower ketones, e.g. $(C_3–C_4)$ketones such as acetone and methyl-ethyl-ketone; cyclic ethers such as dioxane and tetrahydrofuran; glycols and their products of partial etherification, such as ethylene glycol, propylene glycol and ethylene glycol monomethyl ether; lower amides such as dimethylformamide and diethylformamide.

The term "water-immiscible solvent" as used in this application, is intended to have the meaning currently given in the art to this term and refers to solvents that at the conditions of use are slightly miscible or practically immiscible with water in a reasonably wide concentration range, suitable for the intended use.

Examples of water-immiscible organic solvents that can be used in the extraction of the antibiotic substances of the invention from an aqueous phase are: the usual hydrocarbon solvents which may be linear, branched or cyclic such as hexane or cyclohexane; halogenated hydrocarbons such as chloroform, carbon tetrachloride, dichloroethane, fluorobromoethane, dibromoethane, trichloropropane, chlorotrifluorooctane and the like; aromatic hydrocarbons such as benzene, toluene, xylene and the like; esters of at least four carbon atoms, such as ethyl acetate, propyl acetate, ethyl butyrate, and the like; alkanols of at least four carbon atoms which may be linear, branched or cyclic such as butanol, 1-pentanol, 2-pentanol, 3-pentanol, 1-hexanol, 2-hexanol, 3-hexanol, 3,3-dimethyl-l-butanol, 4-methyl-1-pentanol; 3-methyl-1-pentanol, 2,2-dimethyl-3-pentanol, 2,4-dimethyl-3-pentanol, 4,4-dimethyl-2-pentanol, 5-methyl-2-hexanol, 1-heptanol, 2-heptanol, 5-methyl-1-hexanol, 2-ethyl-1-hexanol, 2-methyl-3-hexanol, 1-octanol, 2-octanol, cyclopentanol, 2-cyclopentylethanol, 3-cyclopentyl-1-propanol, cyclohexanol, cycloheptanol, cyclooctanol, 2,3-dimethylcyclohexanol, 4-ethylcyclohexanol, cyclooctylmethanol, 6-methyl-5-hepten-2-ol, 1-nonanol, 2-nonanol, 1-decanol, 2-decanol and 3-decanol; straight or branched alkyl ethers and mixture thereof such as petroleum ether, ethyl ether, propyl ether, butyl ether, etc; and mixtures or functional derivatives thereof.

As known in the art, phase separation may be improved by salting.

When following an extraction an aqueous phase is recovered containing a substantial amount of an organic solvent, it may be convenient to azeotropically distill water from it. Generally, this requires adding a solvent capable of forming minimum azeotropic mixtures with water. The azeotropical distillation of water may be followed by the addition of a precipitating agent to the concentrated organic solution to precipitate the desired product, if necessary. Representative examples of organic solvents capable of forming minimum azeotropic mixtures with water are n-butanol, benzene, toluene, butyl ether, carbon tetrachloride, chloroform, cyclohexane, 2,5-dimethylfuran, hexane and m-xylene; the preferred solvent being n-butanol.

Examples of precipitating agents are petroleum ether, lower alkyl ethers, such as ethyl ether, propyl ether and butyl ether, and lower alkyl ketones such as acetone.

Examples of chromatographic systems that can be conveniently used in the recovery of the antibiotic substances of the invention, are polystyrene or mixed polystyrene-divinylbenzene resins such as Amberlite XAD2 or XAD4 (Rohm and Haas), S112 (The Dow Chemical Co.) and Diaion HP 20 (Mitsubishi); acrylic resins such as XAD7 or XAD8 (Rohm and Haas); polyamides such as polycaprolactames, nylons and cross-linked polyvinylpyrrolidones generally having a pore volume (ml/g) ranging between 1 and 5, surface area (m²/g) ranging between 1 and 100, apparent density (g/ml) ranging between 0.15 and 0.50, average pore diameter (Angstrom units) ranging between 100 and 3000 and particles size distribution where at least 40 percent of the particle size is lower than 300 micrometers, such as Polyamide-CC 6, Polyamide-SC 6, Polyamide-CC 6.6, Polyamide-CC 6AC and Polyamide-SC 6AC (Macherey-Nagel & Co., Germany), the polyvinylpyrrolidone resin PVP-CL (Aldrich Chemie GmbH & Co., KG, Germany), the polyamide resin PA 400 (M. Woelm AG, Germany); and carbon.

Since the antibiotics GE37468 have an acidic character, anion exchange resins can also be utilized for their recovery and purification. Both strongly basic and weakly basic anion exchange resins may be useful. Representative examples of such resins are the following: Dowex® 1×2, Dowex® 1×8 (The Dow Chemical Co.) and Amberlite® IRA 67 (Rohm & Haas).

In the case of polystyrene or acrylic resin a preferred eluent is a polar solvent mixture of water-miscible solvents such as those reported above; in the case of a polyamide resin the eluent is preferably an aqueous mixture of a water-miscible solvent, such as the ones mentioned above, while for carbon a preferred eluent is a lower ketone such as acetone or a lower alcohol such as methanol.

The further purification of a crude preparation of antibiotics GE37468 can be accomplished by any of the known techniques but is preferably conducted by means of chromatographic procedures.

Examples of these chromatographic procedures are those reported above in relation to the recovery step and include also chromatography on stationary phases such as silica gel, allumina, Florisil and the like, with an organic eluting phase made of mixtures of solvents including halogenated hydrocarbons, ethers, higher ketones of the type already mentioned above or reverse-phase chromatography on silanized silica gel having various functional derivatizations and eluting with an aqueous mixture of water-miscible solvents of the kind mentioned above.

Conveniently, also the so-called steric exclusion chromatographic technique can be employed with good purification results. In particular, controlled pore cross-linked dextrans in which most hydroxyl groups have been alkylated, e.g. Sephadex L-20 (Pharmacia LKB Biotechnology, AB), are usefully employed in this technique.

The isolation and separation of the components of a mixture of antibiotics GE37468 may be carried out by using a Medium Pressure Liquid Chromatography (MPLC) system followed by a further purification by preparative or semi-preparative HPLC.

According to a preferred embodiment of this invention, antibiotic GE37468A is separated from antibiotics GE37468B and GE37468C by using a MPLC system with a linear gradient of methanol in methylene chloride which varies from 0% of methanol to 50% of methanol. While the first fractions eluted are enriched n the last two products, as shown by TLC or HPLC analysis, the last fraction essentially contains antibiotic GE37468A. The fractions enriched in GE37468B and GE37468C are submitted to preparative or semi-preparative HPLC for the isolation of the pure individual compounds.

The antibiotic GE37468A obtained from the MPLC system is usually submitted to a further purification by preparative HPLC to yield a high purity sample of such product.

A preferred HPLC technique for the further purification of antibiotic GE37468A is represented by a reverse-phase HPLC using a column with porous and spheric particles of silanized silica gel, e.g. silica gel functionalized with C-18 alkyl groups having a uniform diameter (such as 5 micrometer Ultrasphere ODS Altex; Beckman Co.), a pre-column which is a silica gel functionalized with C-18 alkyl groups (such as RP 18 Brownlee Labs) and an eluent which is a linear gradient mixture of a polar water miscible solvent, such as one of those described above, in an aqueous buffered solution. Preferably this solution is adjusted to pH 6–7. A most preferred eluent is represented by a linear gradient of eluents A and B ranging from 30% to 70%, preferably 40% to 60%, of eluent A wherein eluent A is a mixture of acetonitrile/aqueous buffer, pH 6–7, 80:20 and eluent B is a mixture of acetonitrile/aqueous buffer, pH 6–7, 5:95.

In the HPLC system, for the separation of the two antibiotics GE37468B and GE37468C, it is preferred to utilize the same eluents described above with a linear gradient ranging from 40 to 95%, preferably 50 to 90%.

As usual in this art, the production as well as the recovery and purification steps may be monitored by a variety of analytical procedures including bioassays such as paper disc or agar diffusion assays on sensible microorganisms or TLC or HPLC procedures, which may involve a UV or microbial detention step.

Physico-chemical characteristics of antibiotic GE37468A

A) Ultraviolet absorption spectrum, which is shown in FIG. 1 of the accompanying drawings and exhibits the following absorption maxima:

|  | Lambda max (nm) |
|---|---|
| 0.1M HCl | 307 |
|  | 340 (shoulder) |
| 0.1M KOH | 302 |
|  | 317 (shoulder) |
|  | 334 (shoulder) |
| Phosphate buffer pH 7.4 | 302 |
|  | 338 (shoulder) |
| Methanol | 306 |
|  | 331 (shoulder) |

B) Infrared absorption spectrum in nujol mull which is shown in FIG. 2 of the accompanying drawings and exhibits the following absorption maxima (cm$^{-1}$): 3600; 3100; 2924 (nujol); 2853 (nujol); 1705; 1653; 1514; 1466 (nujol); 1377 (nujol); 1310; 1269; 1200; 1173; 1153; 1101; 1024; 1007; 878; 808; 758; 721 (nujol) 702;

The main functional I.R. absorption bands of this spectrum can be attributed as:

| (cm$^{-1}$) | Assignment |
|---|---|
| 3600, 3100 | NH, OH |
| 1705 (shoulder) | carboxyl (COOH) |
| 1653 | amide I (C=O) |
| 1514 | amide II (NH) |
| 878 | heterocyclic CH |
| 808, 758, 702 | aromatic CH |

C) $^1$H-NMR spectrum which is shown in FIG. 3 and exhibits the following groups of signals (in ppm) at 500 MHz recorded in DMSO-d$_6$ (hexadeuterodimethylsulfoxide) using TMS as the internal standard (0.00 ppm);

[δ, ppm multiplicity, (s, singlet, d=doublet; dd=doublet of doublets; m=multiplet; br s=broad signal)]:

10.08, s; 9.59, s; 9.03, br s; 8.67, s; 8.64, d; 8.57, d; 8.54, d; 8.38, d; 8.19, s; 7.91, s; 7.75, s; 7.30-7.28, m; 7.20, m; 7.18, br s; 7.06, d; 6.78, br s; 6.58, d; 6.49, br s; 6.45, s; 6.06, s; 5.82, s; 5.79, br s; 5.29, m;5.07, m; 4.93, m; 4.87, m; 4.64, d; 3.63, dd; 3.4-3.3, m; 3.19, dd; 2.94, m; 2.73, s; 2.67, m; 2.62, m; 2.11, m;1.98, m; 1.91, m; 1.14, m.

D) $^{13}$C-NMR ($^1$H-decoupled) spectrum which is reported in FIG. 4 of the accompanying drawings exhibiting the following groups of signals ($\delta$, ppm) at 125 MHz in DMSO-$d_6$ with TMS as the internal reference (0.00 ppm) Q means quaternary carbon atoms or C=O groups;

174.4 (Q); 174.0 (Q); 173.0 (Q); 171.6 (Q); 171.4 (Q); 169.3 (Q); 167.6 (Q); 165.0 (Q); 162.3 (Q); 161.3 (Q); 161.2 (Q); 160.8 (Q); 159.0 (Q); 156.0 (Q); 155.7 (Q); 153.9 (Q); 153.3 (Q); 152.1 (Q); 150.5 (Q, 2c); 149.3 (Q); 147.4 (Q); 140.1 (CH); 13 7.3 (Q); 134.7 (Q); 134.6 (Q); 130.7 (2 CH); 129.8 (Q); 129.5 (2 CH); 129.0 (CH); 128.4 (2 CH); 127.4 (Q); 126.8 (CH); 123.9 (CH); 123.1 (Q); 122.3 (CH); 118.7 (CH); 116.7 (CH); 115.1 ( 2 CH); 111.2 ($CH_2$); 105.4 (CH2); 81.9 (CH); 7 7.5 (CH); 66.7 (CH); 54.3 (CH); 52.3 (CH); 48.5 (CH); 42.8 ($CH_2$); 39.0 (CH); 38.5 ($CH_2$); 38.1 ($CH_2$); 37.0 ($CH_2$); 36.3 ($CH_2$); 16.0 ($CH_3$); 11.7 ($CH_3$)

E) Retention-time ($R_t$) of 14.4 min when analyzed by reverse-phase HPLC under the following conditions:

column: Ultrasphere ODS (reverse-phase silanized silica gel; 5 micrometer) Altex (Beckman) 4.6 mm (i.d.)×250 mm pre-column: Brownlee Labs RP 18 (octadecylsilane silica gel; 5 micrometer)

eluent A: acetonitrile:16mM ammonium phosphate 80:20 (v/v), adjusted to pH 6.0 eluent B: acetonitrile:16 mM ammonium phosphate 5:95 (v/v), adjusted to pH 6.0 elution mode: linear gradient of eluent A in eluent B from 10% to 90% in 20 min flow rate: 1.5 ml/min U.V. detector: 230 nm internal standard: antibiotic GE 2270 factor A, EP-A No. 359062 ($R_t$=16.7 min)

F) Elemental analysis, after the sample has been previously dried at about 100° C. under inert atmosphere, which indicates the following composition: carbon, hydrogen, nitrogen, sulfur;

G) $R_f$ value of 0.15 in the following chromatographic system: dichloromethane:methanol, 85:15 (v/v) using silica gel plates (silica gel 60$F_{254}$, Merck Co)

Visualization: U.V. light at 254 nm, yellow spot with iodine vapors or bioautography using B. subtilis ATCC 6633 on minimal Davis medium; internal standard: antibiotic GE 2270 factor A, EP-A No. 359062 ($R_f$ 0.77)

H) FAB-MS analysis showing the lowest mass isotope of the protonated molecular ion at a m/z value corresponding to a molecular weight of 1308.3±0.1 dalton. Upon analysis with a Kratos MS-50TC double focusing mass spectrometer under the following experimental conditions: Xe fast atom bombardment at 8 kV; m-nitrobenzylalcohol matrix; positive ionization mode.

I) An aminoacid analysis of the hydrochloric hydrolysate showing the presence of the following natural aminoacids: cysteine, phenylalanine, tyrosine, and cystine, under the following experimental conditions:

the sample was hydrolyzed at 105° C. for 24 hours in the presence of 6N HCl containing 1% phenol and then derivatized in two steps as follows:

a) formation of the n-propyl esters of the carboxylic acid functions with 2M HCl in anhydrous propanol (90° C., 1 h), and followed by drying under nitrogen;

b) conversion of the free amino groups to amides with trifluoroacetic anhydride/anhydrous dichloromethane, 1/1 (v/v) at 80° C. for 10 min followed by drying under nitrogen; the derivatized residue so obtained was dissolved in dichloromethane and analyzed by GC-MS using a TSQ 700 Finnigan Mat system under the following conditions: column: P-5 fused silica capillary column (25 m×0.32 mm i.d.× 0.17 m; Hewlett & Packard); temperature program 60° C. for 2 min, then 8° C./min.

Antibiotics GE37468B and GE37468C seem to derive from antibiotic GE37468A via hydrolytic degradation. This is supported by the fact that a sample of antibiotic GE37468A, when kept for 6 to 18 hours in an aqueous buffer solution having a pH value between 3 and 4, yields substantial amounts of both antibiotic GE37468B and GE37468C. The physico-chemical characteristics of these two products are as follows:

Physico-Chemical Characteristics of Antibiotic GE37468B

A) Retention-time ($R_t$) of 11.5 min when analyzed by reverse-phase HPLC under the following conditions:

column: Ultrasphere ODS (reverse-phase silanized silica gel; 5 micrometer) Altex (Beckman) 4.6 mm (i.d.)×250 mm eluent A: acetonitrile:16 mM ammonium phosphate 80:20 (v/v), adjusted to pH 6.0 eluent B: acetonitrile:16 mM ammonium phosphate 5:95 (v/v), adjusted to pH 6.0 elution mode: linear gradient of eluent A in eluent B from 40% to 90% in 20 min flow rate: 1.5 ml/min U.V. detector: 230 nm internal standard: Chloramphenicol ($R_t$=4.0 min)

B) FAB-MS analysis showing the lowest mass isotope of the protonated molecular ion at a m/z value corresponding to a molecular weight of 1169.3±0.1 dalton. Upon analysis with a Kratos MS-50TC double focusing mass spectrometer under the following experimental conditions: Xe fast atom bombardment at 8 kV; m-nitrobenzylalcohol matrix; positive ionization mode.

Physico-Chemical Characteristics of Antibiotic GE37468C

A) Retention-time ($R_t$) of 13.0 min when analyzed by reverse-phase HPLC under the following conditions:

column: Ultrasphere ODS (reverse-phase silanized silica gel; 5 micrometer) Altex (Beckman) 4.6 mm (i.d.)×250 mm eluent A: acetonitrile:16 mM ammonium phosphate 80:20 (v/v), adjusted to pH 6.0 eluent B: acetonitrile:16 mM ammonium phosphate 5:95 (v/v), adjusted to pH 6.0 elution mode: linear gradient of eluent A in eluent B from 40% to 90% in 20 min flow rate: 1.5 ml/min U.V. detector: 230 nm internal standard: Chloramphenicol ($R_t$=4.0 min)

B) FAB-MS analysis showing the lowest mass isotope of the protonated molecular ion at a m/z value corresponding to a molecular weight of 1238.3±0.1 dalton. Upon analysis with a Kratos MS-50TC double focusing mass spectrometer under the following experimental conditions: Xe fast atom bombardment at 8 kV; m-nitrobenzylalcohol matrix; positive ionization mode.

On the basis of the above reported physico-chemical data, the following formula I can tentatively be assigned to the antibiotic compound GE37468A:

Analogously, the following formula III may tentatively be assigned to compound GE37468B:

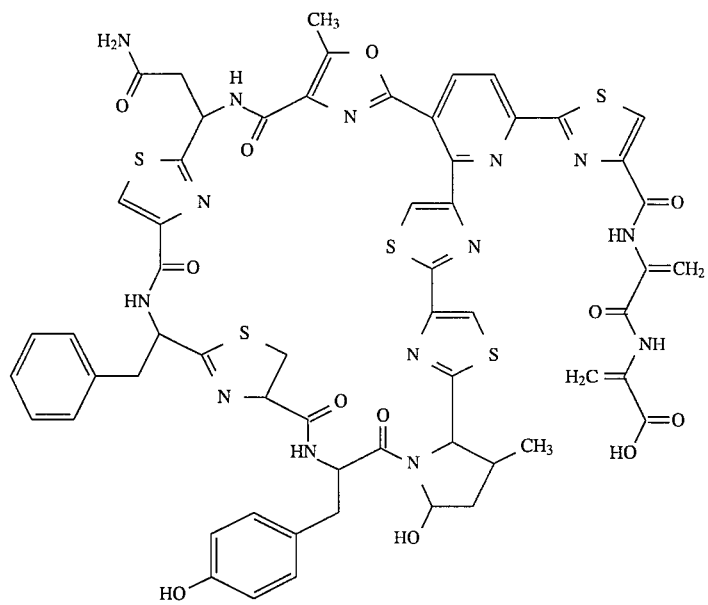

I

As stated above, antibiotics GE37468B and GE37468C seem to derive from antibiotic GE37468A via hydrolytic degradation.

On the basis of the loss of molecular weight of compound GE37468B with respect to GE37468A, determined by FAB-MS analysis, and on the basis of the above surmised formula assigned to compound GE37468A, the following formula II may tentatively be assigned to compound GE37468C:

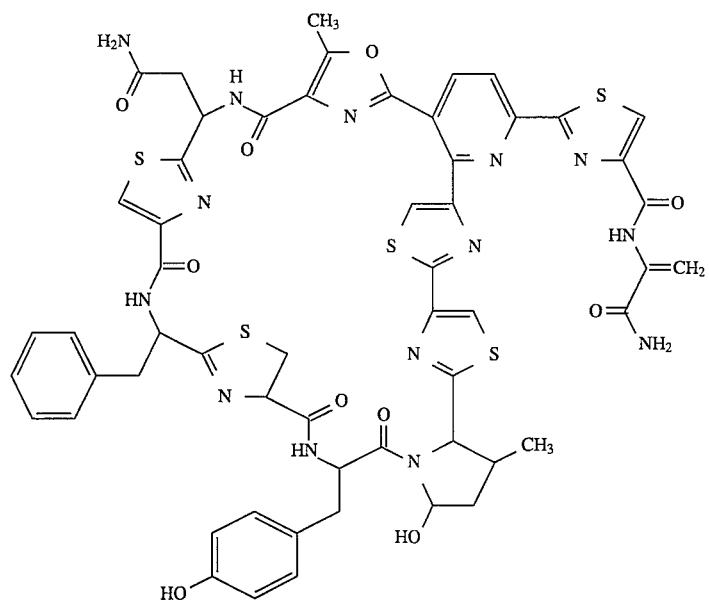

II

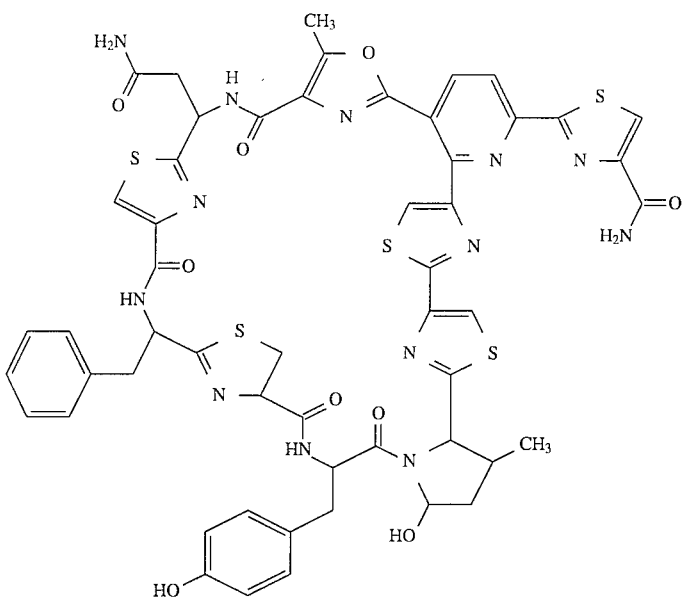

III

Biological Properties and Utilization of Antibiotics GE 37468

The antimicrobial activity of the compounds of this invention was demonstrared by a series of standard in vitro tests.

Minimal inhibitory concentrations (MIC) were determined by broth microdilution. Inocula were $10^4$ CFU/ml, except for C. perfringens, P. acnes and B. fragilis ($10^5$). Incubation times were 20–24 h, except for N. gonorrhoeae, H. influenzae, P. acnes, C. perfringens and B. fragilis (48 h). Incubation was at 37° C. N. gonorrhoeae and H. influenzae were incubated in a 5% $CO_2$ in air; P. acnes, S. perfringens and B. fragilis in $N_2:CO_2:H_2$ (80:10:10). The media used were: Iso-Sensitest broth (Oxoid) (staphylococci, Enterococcus faecalis, Escherichia coli, Pseudomonas aeruginosa, Proteus vulgaris); GC Base broth (Difco) +1% (v/v) IsoVitalex (BBL) (N. gonorrhoeae); Brain Heart Infusion broth (Difco) +1% (v/v) Supplement C (Difco) (H. influenzae); Wilkins-Chalgren broth (Difco) (P. acnes, C. perfringens, B. fragilis), phosphate buffered Yeast Nitrogen Base broth (Difco) containing glucose (1% w/v) and L-asparagine (0.15% w/v) (C. albicans).

The following Table IV reports the results of the above mentioned tests for antibiotics GE37468A, GE37468B, and GE37468C.

TABLE IV

| Strain | Compound M.I.C. (microgram/ml) | | |
|---|---|---|---|
| | GE37468A | GE37468B | GE37468C |
| Staphylococcus aureus L165 | 0.03 | 0.03 | 0.03 |
| Staphylococcus aureus Smith | 0.016 | 0.03 | 0.03 |
| Staphylococcus epidermidis ATCC 12228 | 0.25 | 0.06 | 0.25 |
| Staphylococcus haemolyticus L602 | 0.13 | 0.13 | 0.13 |
| Enterococcus faecalis ATCC 7080 | 0.016 | 0.03 | 0.03 |
| Clostridium perfringens L290 | 0.002 | 0.016 | 0.016 |
| Propionibacterium acnes ATCC 6919 | 0.004 | 0.016 | 0.016 |
| Bacteroides fragiles ATCC 25285 | 2 | >128 | >128 |
| Neisseria gonorrhoeae L997 | 64 | >128 | >128 |
| Haemophilus influenzae ATCC 19418 | >128 | >128 | >128 |
| Escherichia coli L47 | >128 | >128 | >128 |
| Pseudomonas aeruginosa ATCC 10145 | >128 | >128 | >128 |
| Proteus vulgaris ATCC 881 | >128 | >128 | >128 |
| Candida albicans L145 | >128 | >128 | >128 |

The antimicrobial activity of antibiotic GE37468A was also confirmed in experimental septicemia in mice.

Groups of five CD1 mice of both sexes (Charles River, average weight 18–22 g) were infected intraperitoneally with $10^6$ CFU/mouse of Staphylococcus aureus Smith suspended in 0.5 ml of 5% bacteriological mucin (Difco). The test compound was administered intravenously once, immediately after infection, in a sterile solution containing 10% dimethylsulfoxide, 10% Cremophor EL®, 20% 0.07 M phosphate buffer (pH 8), 60% glucose solution (5%).

The $ED_{50}$, calculated by the Spearman and Kaerber method from the percentage of animals at each dose surviving at day 7 after infection, was 3.2 mg/kg.

In view of their properties, the compounds of the invention can be used as active ingredient in the preparation of medicaments for human or animal treatment.

In particular, antibiotics GE37468A, GE37468B and GE37468C are antimicrobial agents mainly active against gram positive bacteria and gram positive as well as gram negative anaerobes.

The main therapeutic indication of the antibiotic substances of the invention is thus in the treatment of infections related to the presence of a microorganism susceptible to it.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compounds of the invention can be administered as such or in admixture with pharmaceutically acceptable carriers and can also be administered in conjunction with other antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

A preferred pharmaceutical formulation is represented by a formulation suitable for a topical application on an intact or damaged skin or mucous membrane. Examples of such formulations are powders, ointments, creams and lotions. The excipients in these formulations are the usual pharmaceutically acceptable vehicles such oleaginous ointment bases (e.g. cetyl esters wax, oleic acid, olive oil, paraffin, spermaceti, starch glycerite); absorbent ointment bases (e.g. anhydrous lanolin, hydrophilic petrolatum), emulsion ointment bases (e.g. cetyl alcohol, glyceryl monostearate, lanolin, stearic acid), water-soluble ointment bases (e.g. glycol ethers and their derivatives which include polyethylene glycols, poly-(oxy-1,2-ethanediyl) -alpha-hydro-omega-hydroxy-octadecanoate, polysorbates, and polyethylene glycols mono-stearates).

These formulations may contain other known excipients, such as preservatives and are prepared as known in the art and reported in reference handbooks such as Remington's Pharmaceutical Sciences, Seventeenth edition, 1985, Mack Publishing Co.

The compounds of the invention can also be formulated into formulations suitable for parenteral administration according to procedures known per se in the art and reported in reference books such as the one mentioned above.

For instance, a compound of the invention is formulated with a solubilizing agent such as polypropylene glycol or dimethylacetamide and a surface-active agent such as polyoxyethylene sorbitan mono-oleate or polyethoxylated castor oil in steril water for injection.

An example of a typical formulation for parenteral administration contains 10 mg of antibiotic GE37468A, B or C for ml of final preparation, 10–20% of a surface-active agent which may be a polyoxyethylene sorbitan fatty acid ester, a polyoxyethylene castor oil derivative or a polyoxyethylene hydrogenated castor oil derivative and 0–20%, and preferably 10–20% of a solubilizing agent such as propylene glycol, dimethylacetamide, dimethylformamide, ter-butyl-N-hydroxycarmabate, 1,2-, 1,3-, or 1,4-butandiol, ethyl oleate, tetrahydrofurfuryl-polyethylene-glycol 200, dimethyl isosorbide, benzyl alcohol and the like. A preferred solubilizing agent is propylene glycol.

Polyoxyethylene sorbitan fatty acid esters are commercially available and some of them are traded under the trade name "Tween". They are also known with the non-proprietary name of "polysorbates". Examples of them are polysorbate 20, 21, 40, 60, 61, 65, 80, 81 and 85. Preferred for use in the formulations of the invention is polysorbate 80 (sorbitan mono- 9-octadecanoate, poly(oxy-1,2-ethanediyl-)derivatives).

Polyoxyethylene castor oils and polyoxyethylene hydrogenated castor oils are also commercially available. Some of them are traded with the trade name "Cremophor". Examples of such compounds are those known as Cremophor® EL (polyethoxylated castor oil), Cremophor® RH 40 (polyethoxylated hydrogenated castor oil), Cremophor® RH 60 (PEG 60 hydrogenated castor oil) or Emulphor® EL-719 (polyoxyethylated vegetable oil).

Preferably, a formulation for injection should have a p in the range of 7±0.5. If necessary, it might be advisable to adjust the pH of the preparation with a suitable buffering agent. Conveniently, TRIS (i.e. trihydroxymethylaminomethane) or phosphate can be used as buffering agents.

A preferred formulation for parenteral administration includes the following excipients: Cremophor® EL (polyoxyl 35 castor oil USP/NF) 20%, propylene glycol from 5 to 20%, preferably 10–20%.

Generally, these formulations can be prepared by dissolving the active ingredient into the organic solvent, then adding, with sitting, the surface active ingredient, and finally diluting to the desired volume with sterile water for injection.

Other excipients, such as preservative or stabilizing agents can be added as known in the art.

An example of a parenteral formulation is the following:

| | |
|---|---|
| antibiotic GE37468A, B or C | 10 mg |
| PEG 40 castor oil (Cremophor EL) | 0.2 ml |
| propylene glycol | 0.2 ml |
| methyl parahydroxybenzoate | 0.5 mg |
| propyl parahydroxybenzoate | 0.05 mg |
| water for injection q.s. | 1 ml |

Alternatively, the active ingredient may be prepared as a lyophilized powder for reconstitution before use.

If the lyophilized material is prepared starting from a mixture containing the active ingredient and the surfactant, such as polyethylene glycol 60 hydrogenated castor oil, it can conveniently be reconstituted with the aqueous medium alone, without addition of an organic solvent.

Optionally, a common lyophilization aid can be added, if necessary, to obtain a lyophilized material in powder form.

Preferably, all these formulations are used for i.v. administration in the treatment of any infection involving a microorganism susceptible to the antibiotic of the invention.

In the treatment of pseudomembranous colitis or other diseases attributable to the presence of anaerobes in the gastrointestinal tract, an effective dose of the compound of the invention may be administered orally in a suitable pharmaceutical form such as a capsule, a tablet or an aqueous suspension.

The dosage of the active ingredient depends on many factors which include type, age and conditions of the patient, specific active ingredient and formulation selected for the administration, administration schedule, etc.

In general, effective antimicrobial dosages are employed per single unit dosage form.

Repeated applications/administrations, e.g. from to 6 times a day, are in general preferred. An effective dosage may be in general in the range 0.5–500 mg/kg body weight/day.

A preferred topic preparation is an ointment containing from 1% to 10% of a compound of the present invention.

Anyway, the prescribing physician will be able to determine the optimal dosage for a given patient in a given situation.

Besides their use as medicaments in human and veterinary therapy, the compounds of the invention can also be used as animal growth promoters.

For this purpose, a compound of the invention is administered orally in a suitable feed. The exact concentration employed is that which is required to provide for the active agent in a growth promotant effective amount when normal amounts of feed are consumed.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and CO., S. Francisco, USA, 1969 or "Livestock Feeds and Feeding" O and B books, Corvallis, Oreg., USA, 1977).

The following examples further illustrate the invention and have not to be interpreted as limiting it in any way.

EXAMPLE 1

Production of Antibiotics GE37468

A culture of *Streptomyces sp.* GE 37468 ATCC 55365 is grown on an oatmeal agar slant for four days at 28°–30° C. and then used to inoculate 500 ml flasks containing 100 ml of a seed medium of the following composition:

| Dextrose | 20 g/l |
|---|---|
| Yeast extract | 2 g/l |
| Soybean meal | 8 g/l |
| Calcium carbonate | 4 g/l |
| Sodium chloride | 1 g/l |
| Distilled water q.s. | 100 ml |
| (adjusted to pH 7.0 before sterilization) | |

The flask is incubated on a rotary shaker (200 rpm) at 28°–30° C. for 26 h. The obtained culture is then used to inoculate a jar fermenter containing 4 liters of the same medium and the culture is incubated at 28°–30° C. for 24 hours with stirring (about 900 rpm) and aeration (about 0.5 standard liter of air per volume per minute).

The obtained broth is transferred to a fermenter containing 200 l of the following production medium:

| Sorbitol | 20 g/l |
|---|---|
| Yeast extract | 2 g/l |
| Soybean meal | 8 g/l |
| Calcium carbonate | 4 g/l |
| Sodium chloride | 1 g/l |
| Distilled water q.s. | 100 ml |
| (adjusted to pH 7.0 before sterilization) | | and incubated for about 72 hours at 28°–30° C. controlling the pH between 7.0 and 7.5 by addition of sulphuric acid.

Antibiotic production is monitored by HPLC or agar diffusion assay using *B. subtilis* ATCC 6633 grown on minimum Davis medium. The inhibition zones are evaluated after incubation overnight at 35° C.

EXAMPLE 2

Recovery of Antibiotics GE37468

The harvested broth deriving from repeated fermentation operations as described in Example 1, are pooled (300 l) and filtered in the presence of a filter aid (Clarcell).

Most of the fermentation product is recovered from the mycelium.

The mycelium is extracted with 100 l of acetone and the extract is concentrated under reduced pressure to give an aqueous residue which is extracted with n-butanol (7 l ). A solid containing antibiotics GE37468 (13.5 g) is precipitated from the concentrated organic phase upon addition of petroleum ether.

This solid (13.3 g) is suspended in 3 l of ammonium formate buffer (16 mM, pH 6.0) and extracted three times with an equal volume of ethyl acetate. The water solution is then adjusted to pH 4.5 with HCl 1 N and extracted with ethyl acetate (3 l ). The organic phases are pooled and concentrated under reduced pressure.

The crude antibiotics GE 37468 (3.4 g) are recovered upon precipitation with petroleum ether.

EXAMPLE 3

Purification of Antibiotics GE 37468 on Sephadex LH-20

The crude antibiotics GE 37468 (3.3 g), obtained as described in Example 2, are suspended in methanol containing 10% of tetrahydrofuran. The suspension is applied to a chromatographic column containing a controlled pore cross-linked dextran (Sephadex LH-20, Pharmacia LKB Biotechnology AB) swollen in methanol (1.5 l).The column is developed with methanol.

Fractions are collected, analyzed by TLC, HPLC or by agar diffusion assay against *B. subtilis* ATCC 6633 and are pooled according to their antibiotics content. The pooled fractions containing antibiotics GE 37468 are concentrated under reduced pressure.

Partially purified antibiotics GE 37468 (1.3 g) are recovered from the oily residue upon addition of diethyl ether.

EXAMPLE 4

Isolation and Purification of Antibiotic GE 37468A by MPLC

The solid obtained as described in Example 3 (1.24 g) is dissolved in tetrahydrofuran and concentrated under reduced pressure in the presence of silica gel (230–400 mesh). The obtained solid residue is collected and applied to a chromatography column (45 cm×7 cm) containing silica gel (230–400 mesh) swollen in methylene chloride ($CH_2Cl_2$). The column is developed using a Medium Pressure Liquid Chromatography (MPLC) system (Model B-681 and B-687, Büchi Laboratory-Techniques Ltd.) with a mixture of methanol and methylene chloride linear gradient 0 to 10% (v/v) methanol in 10 minutes, then 10 to 50% (v/v) methanol in 110 minutes) at a flow rate of 100 ml/min.

The collected fractions are analyzed by TLC, HPLC or by agar diffusion assay against *B. subtilis* ATCC 6633.

Fractions 60 to 83 are pooled according to their antibiotic content and are concentrated under reduced pressure to give an oily residue which is solubilized with tetrahydrofuran.

From this solution, antibiotic GE37468A (500 mg) is precipitated by adding petroleum ether.

EXAMPLE 5

Further Purification of Antibiotic GE 37468A by Preparative HPLC

A high purity sample of antibiotic GE37468A can be obtained by HPLC purification, according to the following procedure:

A portion (9 mg) of the precipitate obtained as described in Example 4 is dissolved in 1 ml of acetonitrile and 1 ml of 16 mM ammonium formate buffer (pH 7.0) and is further purified by preparative HPLC on a silanized silica gel column (Lichrosorb RP 18, 7 micrometer, 250 mm×25 mm, Merck, Darmstadt).

Elution is made with a linear gradient of phase A and phase B (45% to 55% (v/v) phase A in 20 min) at a flow rate of 12 ml/min. Phase A is a mixture of acetonitrile and 16 mM ammonium formate buffer 80/20 (v/v), adjusted to pH 7, while phase B is a mixture of acetonitrile and 16 mM ammonium formate, 5/95 (v/v), adjusted to pH 7.

UV detection is set at 230 nm. The fractions of 8 subsequent chromatographic runs having homogeneous content are pooled and concentrated under reduced pressure to remove acetonitrile. The solution containing pure antibiotic GE37468A is extracted three times with an equal volume of ethyl acetate. The organic phases are pooled and concentrated to dryness under reduced pressure. The residue is dissolved in DMSO and freeze dried to yield 34 mg of pure antibiotic GE 37468A.

EXAMPLE 6

Separation and Purification of Antibiotics GE37468B and GE37468C

During the work-up of the fermentation product, partial degradation of GE37468A is observed, resulting in the formation of substantial amounts of two hydrolysis products.

The first ten fractions obtained by the chromatographic procedure described in Example 4 are enriched in these hydrolysis products, as shown by TLC and HPLC analysis. These fractions are pooled and concentrated under reduced pressure to give an oily residue from which a mixture of the two hydrolysis products is precipitated by addition of petroleum ether.

The two products are isolated and purified by preparative HPLC. A portion (6 mg) of the mixture is dissolved in 0.5 ml of acetonitrile and 0.5 ml of 16 mM ammonium formate buffer (pH 6.2) and is injected in five runs on a silanized silica gel column (Ultrasphere ODS, 5 micrometer, 250×4.6 mm, Altex, Beckman).

Elution is made with a linear gradient of phase A and phase B (50% to 90% phase A in 20 min) at a flow rate of 1.5 ml/min. Phase A is a mixture of acetonitrile and 16 mM ammonium formate buffer 80/20 (v/v), adjusted to pH 6.2, while phase B is a mixture of acetonitrile and 16 mM ammonium formate, 5/95 (v/v), adjusted to pH 6.2.

U.V. detection is set at 230 nm. The fractions corresponding to a retention time ($R_t$) of 11 to 12.5 min of each chromatographic run are collected and pooled. After removal of acetonitrile by distillation under reduced pressure a white solid precipitates from the resulting aqueous solution. The solid is collected, washed with water and dried, yielding 1.5 mg of pure GE37468B.

The fractions corresponding to a retention time ($R_t$) of 13 to 13.5 min of each chromatographic run are also collected and pooled. Following a procedure analogous to that described above, 1.0 mg of pure GE37468C is obtained.

BRIEF DESCRIPTION OF THE DRAWINGS

♦ refers to the assay in $CH_3OH$
▲ refers to the assay in 0.1 M HCl
● refers to the assay in phosphate buffer pH 7.4
■ refers to the assay in 0.1 M KOH

Figure 1:
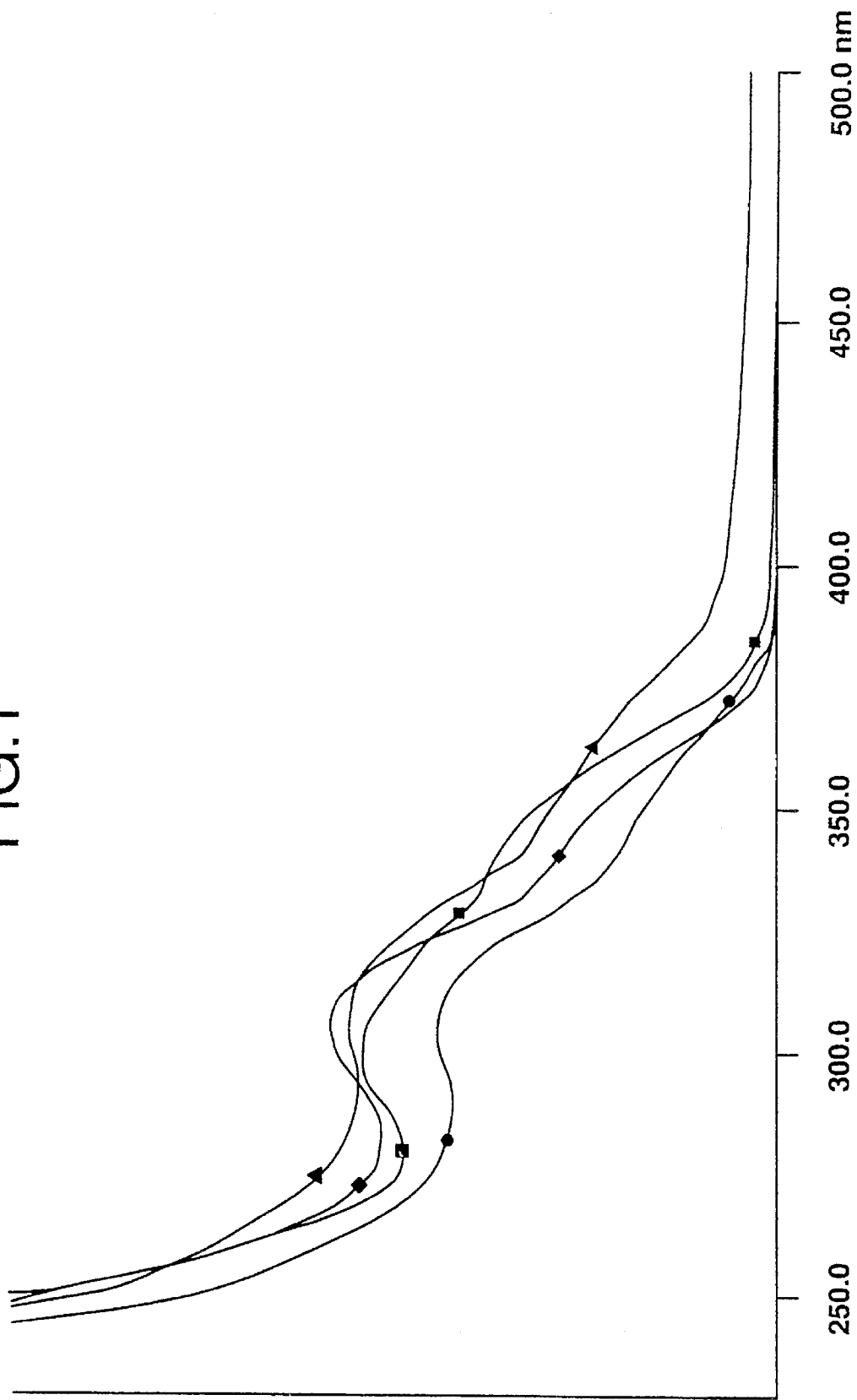
FIG. 1 reports the UV spectrum of antibiotic GE37468A. The correspondence between the symbols and the employed solvents is the following.
Figure 2:
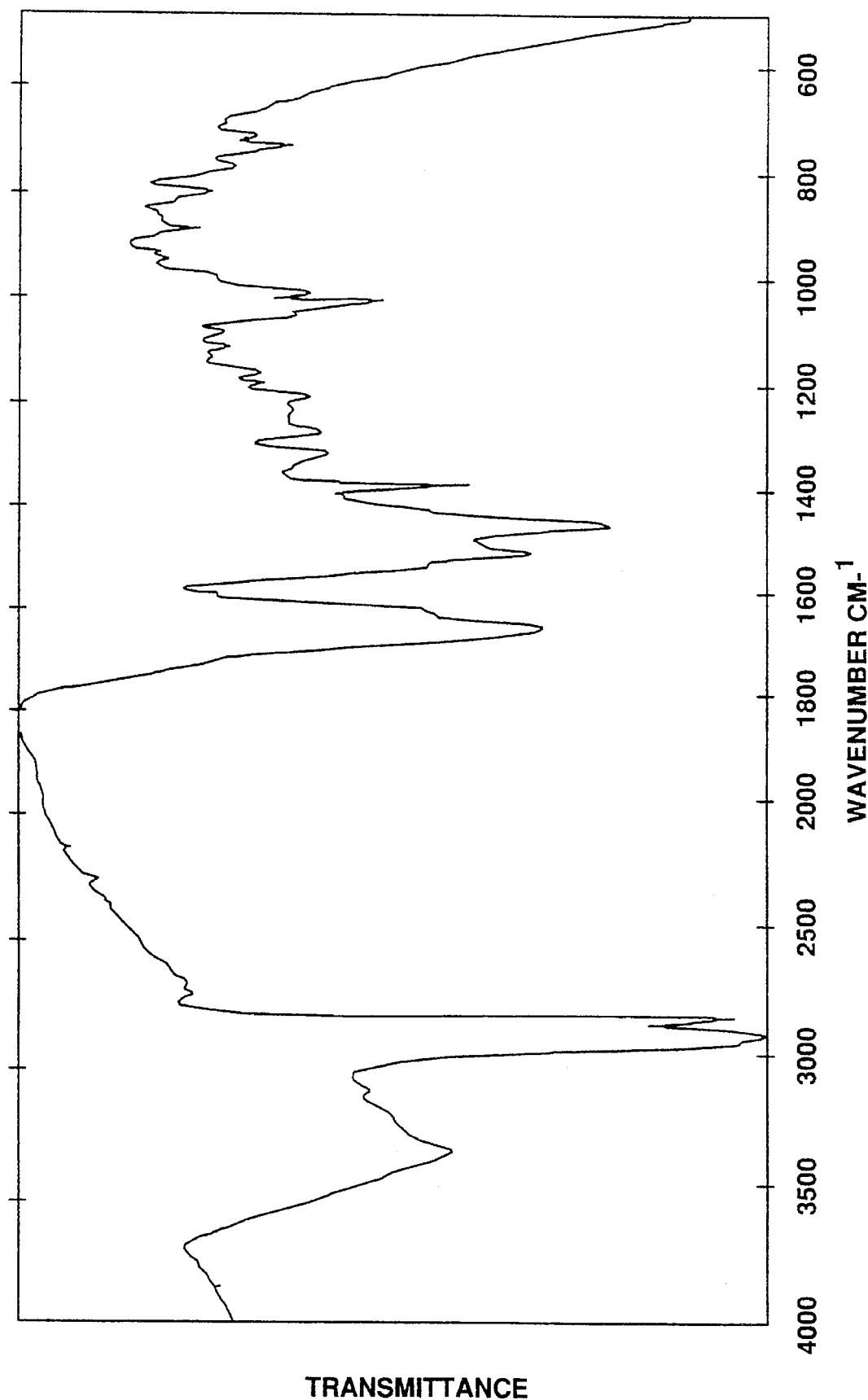
FIG. 2 represents the I.R. absorption spectrum of antibiotic GE37468A in nujol mull
Figure 3:
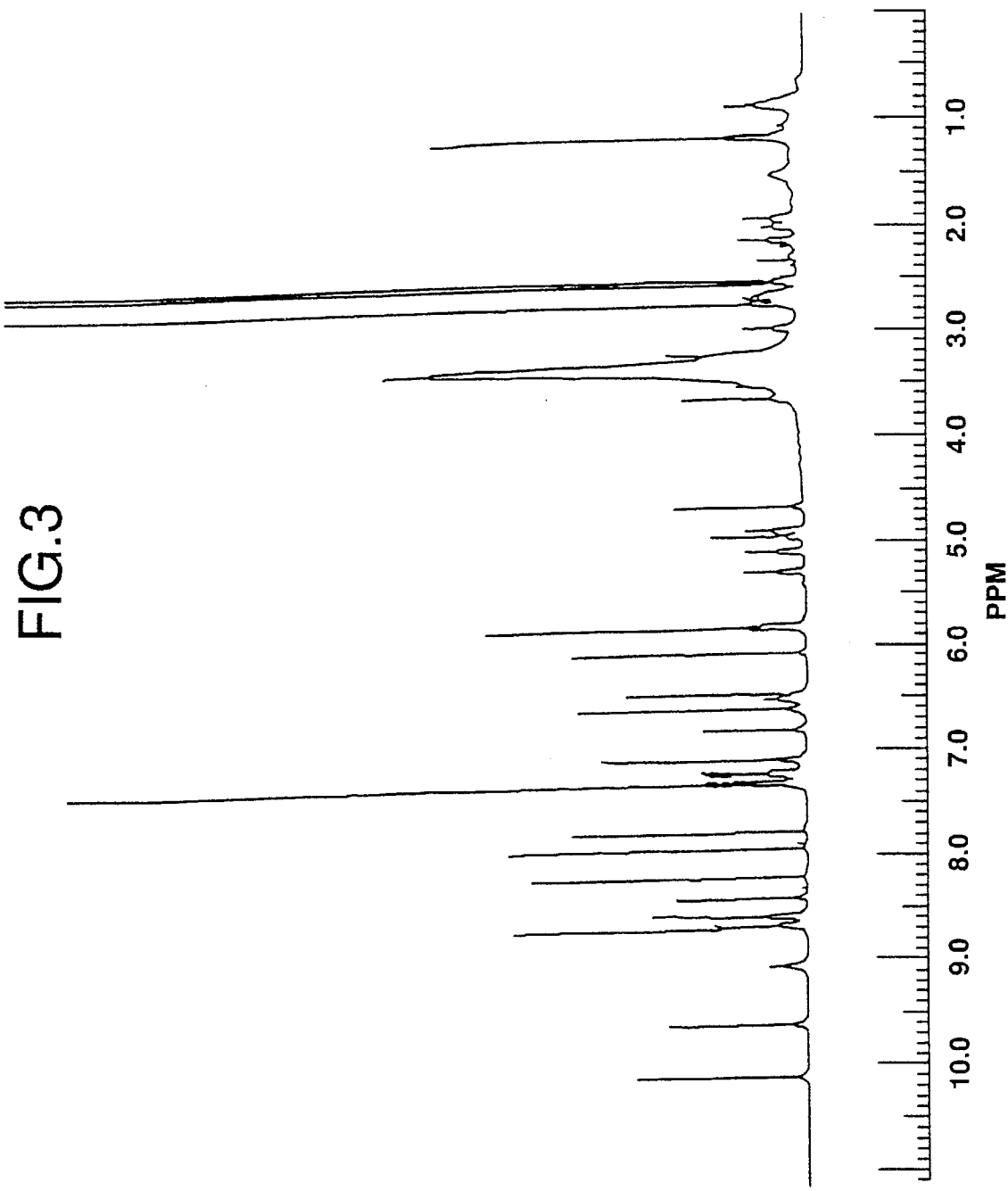
FIG. 3 represents the $^1$H-NMR of antibiotic GE37468A measured at 500 MHz in DMSO-$d_6$
Figure 4:
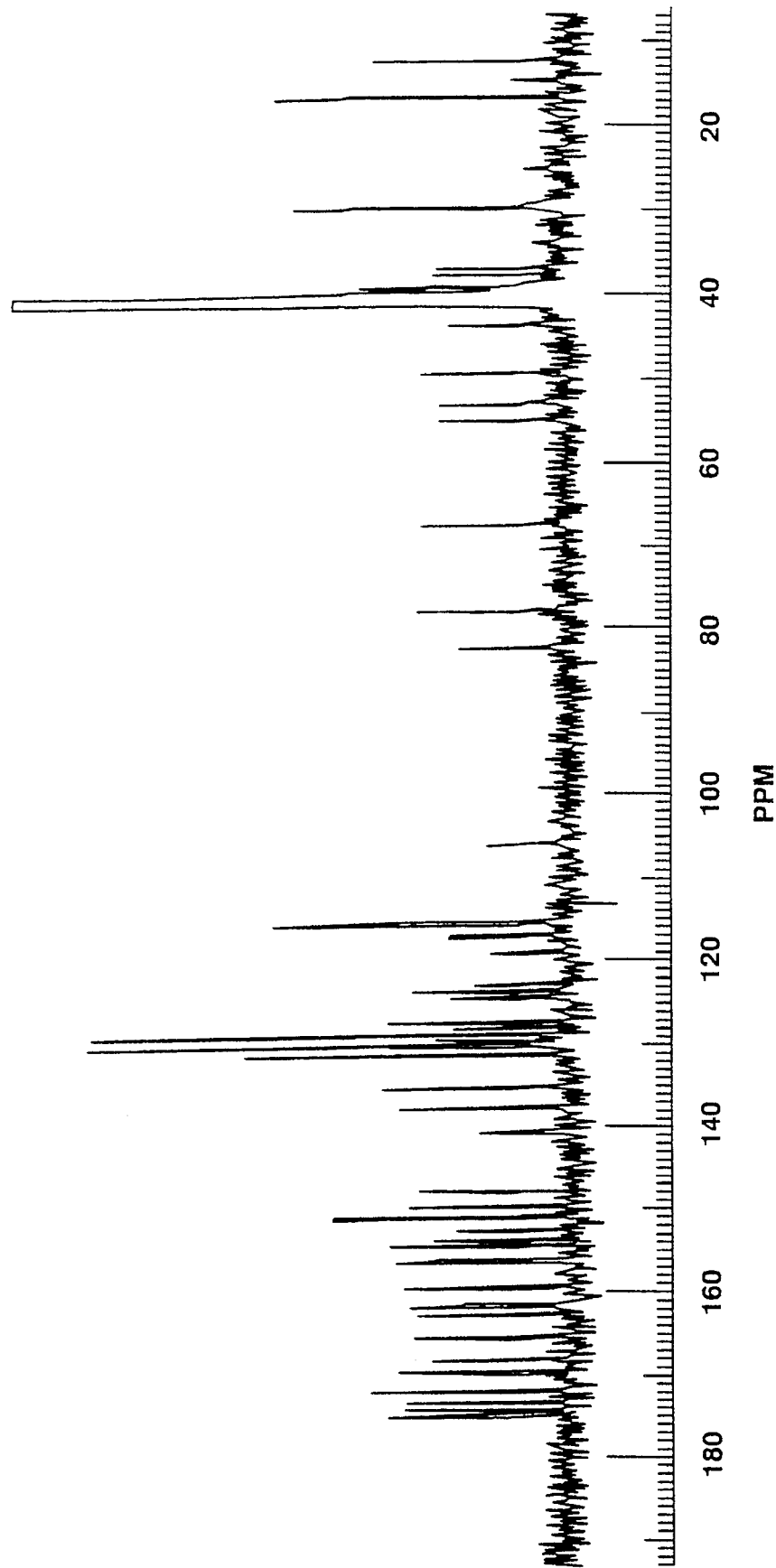
FIG. 4 represents the $^{13}$C-NMR of antibiotic GE37468A at 125 MHz in DMSO-$d_6$.

We claim:

1. An antibiotic selected from antibiotic GE37468A, antibiotic GE37468B, and antibiotic GE37468C, or their salts with bases having, in the non-salt form, the following respective characteristics:

Antibiotic GE37468A

A) Ultraviolet absorption spectrum exhibiting the following absorption maxima:
Lambda max (nm)
0.1 M HCl 307
340 (shoulder)
0.1 M KOH 302
317 (shoulder)
334 (shoulder)
Phosphate buffer pH 7.4 302
338 (shoulder)
Methanol 306
331 (shoulder)

B) Infrared absorption spectrum in nujol mull exhibiting the following absorption maxima ($cm^{-1}$): 600; 3100; 2924 (nujol); 2853 (nujol); 1705; 1653; 514; 1466 (nujol); 1377 (nujol); 1310; 1269; 1200; 173; 1153; 1101; 1024; 1007; 878; 808; 758; 721 (nujol) 702;

C) $^1$H-NMR spectrum exhibiting the following groups of signals (in ppm) at 500 MHz recorded in DMSO-$d_6$ (hexadeuterodimethylsulfoxide) using TMS as the internal standard (0.00 ppm);

[δ, ppm multiplicity, (s, singlet, d=doublet; dd =doublet of doublets; m=multiplet; br s=broad signal)]:
10.08, s; 9.59, s; 9.03, br s; 8.67, s; 8.64, d; 8.57, d; 8.54, d; 8.38, d; 8.19, s; 7.91, s; 7.75, s; 7.30–7.28, m; 7.20, m; 7.18, br s; 7–06, d; 6.78, br s; 6.58, d; 6.49, br s; 6.45, s; 6.06, s; 5.82, s; 5.79, br s; 5.29, m;5.07, m; 4.93, m; 4.87, m; 4.64, d; 3.63, dd; 3.4–3.3, m; 3.19, dd; 2.94, m; 2.73, s; 2.67, m; 2.62, m; 2.11, m;1.98, m; 1.91, m; 1.14, m;

D) $^{13}$C-NMR ($^1$H-decoupled) spectrum exhibiting the following groups of signals (δ, ppm) at 125 MHz in DMSO-$d_6$ with TMS as the internal reference (0.00 ppm); Q means quaternary carbon atoms or C=O groups;

174.4 (Q); 174.0 (Q); 173.0 (Q); 171.6 (Q); 171.4 (Q); 169.3 (Q); 167.6 (Q); 165.0 (Q); 162.3 (Q); 161.3 (Q

); 161.2 (Q); 160.8 (Q); 159.0 (Q); 156.0 (Q); 155.7 (Q); 153.9 (Q); 153.3 (Q); 152.1 (Q); 150.5 (Q, 2C); 149.3 (Q); 147.4 (Q); 140.1 (CH); 137.3 (Q); 134.7 (Q); 134.6 (Q); 130.7 (2 CH); 129.8 (Q); 129.5 (2 CH); 129.0 (CH); 128.4 (2 CH); 127.4 (Q); 126.8 (CH); 123.9 (C); 123.1 (Q); 122.3 (CH); 118.7 (CH); 116.7 (CH); 115.1 (2 CH); 111.2 ($CH_2$); 105.4 ($CH_2$); 81.9 (CH); 77.5 (CH); 66.7 (CH); 54.3 (CH); 52.3 (CH); 48.5 (CH); 42.8 ($CH_2$); 39.0 (CH); 38.5 (CH2); 38.1 ($CH_2$); 37.0 ($CH_2$); 36.3 ($CH_2$); 16.0 ($CH_3$); 11.7 ($CH_3$)

E) Retention-time ($R_t$) of 14.4 min when analyzed by reverse-phase HPLC under the following conditions:
column: Ultrasphere ODS (reverse-phase silanized silica gel; 5 micrometer) Altex (Beckman) 4.6 mm (i.d.)×250 mm
pre-column: Brownlee Labs RP 18 (octadecylsilane silica gel; 5 micrometer)
eluent A: acetonitrile:16mM ammonium phosphate 80:20 (v/v), adjusted to pH 6.0
eluent B: acetonitrile:16mM ammonium phosphate 5:95 (v/v), adjusted to pH 6.0
elution mode: linear gradient of eluent A in eluent B from 10% to 90% in 20 min
flow rate: 1.5 ml/min
U.V. detector: 230 nm
internal standard: antibiotic GE 2270 factor A, ($R_t$=16.7 min)

F) Elemental analysis, of a sample dried at about 100° C. under inert atmosphere, indicating the following composition: carbon, hydrogen, nitrogen, sulfur;

G) $R_f$ value of 0.15 in the following chromatographic system: dichloromethane:methanol, 85:15 (v/v) using silica gel plates (silica gel $60F_{254}$, Merck Co)
Visualization: U.V. light at 254 nm, yellow spot with iodine vapors or bioautography using *B. subtilis* ATCC 6633 on minimal Davis medium; internal standard: antibiotic GE 2270 factor A, ($R_f$ 0.77)

H) FAB-MS analysis showing the lowest mass isotope of the protonated molecular ion at a m/z value corresponding to a molecular wight of 1308.3±0.1 dalton. Upon analysis with a Kratos MS-50TC double focusing mass spectrometer under the following experimental conditions: Xe fast atom bombardment at 8 kV; m-nitrobenzylalcohol matrix; positive ionization mode I) An aminoacid analysis of the hydrochloric hydrolysate showing the presence of the following natural aminoacids: cysteine, phenylalanine, tyrosine, and cystine;

Antibiotic GE37468B

A) Retention-time ($R_t$) of 11.5 min when analyzed by reverse-phase HPLC under the following conditions:
column: Ultrasphere ODS (reverse-phase silanized silica gel; 5 micrometer) Altex (Beckman) 4.6 mm (i.d.)×250 mm
eluent A: acetonitrile:16 mM ammonium phosphate 80:20 (v/v), adjusted to pH 6.0
eluent B: acetonitrile:16 mM ammonium phosphate 5:95 (v/v), adjusted to pH 6.0
elution mode: linear gradient of eluent A in eluent B from 40% to 90% in 20 min
flow rate: 1.5 ml/min
U.V. detector: 230 nm
internal standard: Chloramphenicol ($R_t$=4.0 min)

B) FAB-MS analysis showing the lowest mass isotope of the protonated molecular ion at a m/z value corresponding to a molecular weight of 1169.3±0.1 dalton. All other peaks above 800 m/z mass units (not counting isotope peaks) in the spectrum resulting lower than 20% of the molecular ion, upon analysis with a Kratos MS-50TC double focusing mass spectrometer under the following experimental conditions: Xe fast atom bombardment at 8 kV; m-nitrobenzylalcohol matrix; positive ionization mode;

Antibiotic GE37468C

A) Retention-time ($R_t$) of 13.0 min when analyzed by reverse-phase HPLC under the following conditions:
column: Ultrasphere ODS (reverse-phase silanized silica gel; 5 micrometer) Altex (Beckman) 4.6 mm (i.d.)×250 mm
eluent A: acetonitrile:16 mM ammonium phosphate 80:20 (v/v), adjusted to pH 6.0
eluent B: acetonitrile:16 mM ammonium phosphate 5:95 (v/v), adjusted to pH 6.0
elution mode: linear gradient of eluent A in eluent B from 40% to 90% in 20 min
flow rate: 1.5 ml/min
U.V. detector: 230 nm
internal standard: Chloramphenicol ($R_t$=4.0 min)

B) FAB-MS analysis showing the lowest mass isotope of the protonated molecular ion at a m/z value corresponding to a molecular weight of 1238.3±0.1 dalton. Upon analysis with a Kratos MS-50TC double focusing mass spectrometer under the following experimental conditions: Xe fast atom bombardment at 8 kV; m-nitrobenzylalcohol matrix; positive ionization mode.

2. Antibiotic GE37468A and the pharmaceutically acceptable salts thereof having, in the non-salt form, the following formula I:

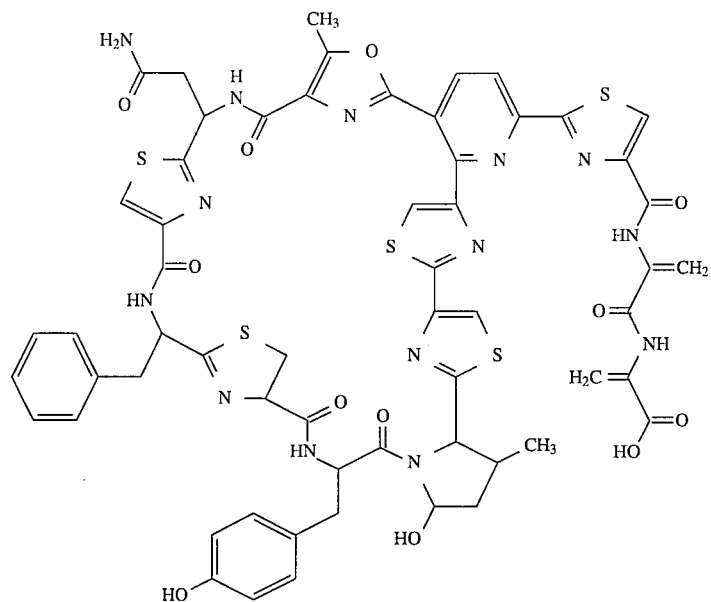
3. Antibiotic GE37468C and the pharmaceutically acceptable salts thereof having, in the non-salt form, the following formula II:
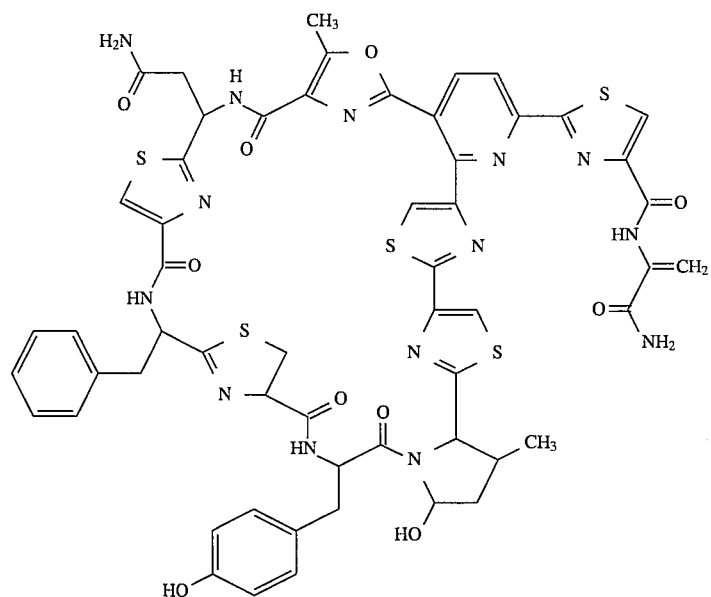
4. Antibiotic GE37468B and the pharmaceutically acceptable salts thereof having, in the non-salt form, the following formula III:

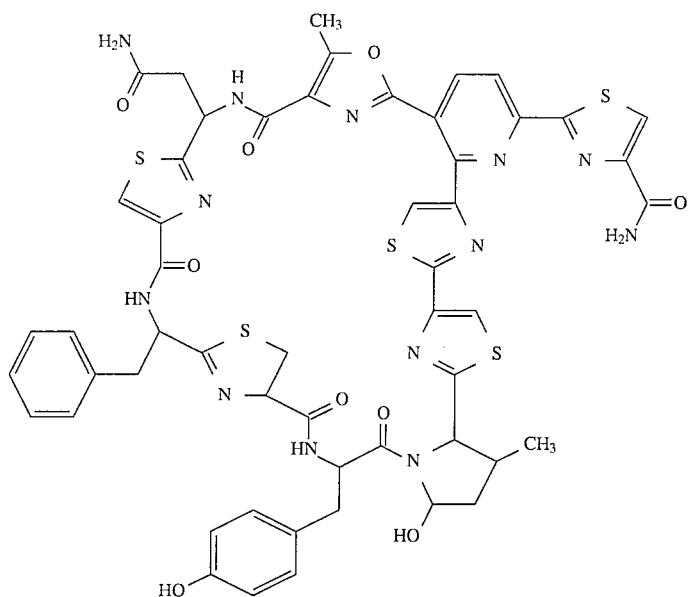
II
5. A method for the treatment of bacterial infections comprising administering a compound according to any one of claims 1, 2, 3, or 4 to a patient in need thereof.
* * * * *